United States Patent
Scholey et al.

(10) Patent No.: US 8,968,800 B2
(45) Date of Patent: Mar. 3, 2015

(54) APPLICATION OF AMERICAN GINSENG TO ENHANCE NEUROCOGNITIVE FUNCTION

(75) Inventors: Andrew Scholey, Melbourne (AU); Alvin Ibarra, Hoboken, NJ (US); Kan He, Rancho Palos Verdes, CA (US); Marc Roller, Morieres les Avingnon (FR); Jacques Dikansky, Avignon (FR)

(73) Assignee: Naturex, S.A., Montfavet, Avignon (FR)

( * ) Notice: Subject to any disclaimer, the term of this patent is extended or adjusted under 35 U.S.C. 154(b) by 650 days.

(21) Appl. No.: 13/288,745

(22) Filed: Nov. 3, 2011

(65) Prior Publication Data

US 2012/0046239 A1    Feb. 23, 2012

Related U.S. Application Data

(62) Division of application No. 12/435,343, filed on May 4, 2009, now abandoned.

(51) Int. Cl.
    *A61K 36/258*    (2006.01)
(52) U.S. Cl.
    CPC ................................ *A61K 36/258* (2013.01)
    USPC ........................................................ 424/728

(58) Field of Classification Search
    CPC ...................................................... A61K 36/258
    USPC ............................................................. 424/728
    See application file for complete search history.

(56) References Cited

U.S. PATENT DOCUMENTS

| | | | |
|---|---|---|---|
| 6,083,932 A * | 7/2000 | Pang et al. | 514/54 |
| 2006/0257502 A1 | 11/2006 | Liu et al. | |
| 2008/0085888 A1 * | 4/2008 | Breining et al. | 514/211.13 |

FOREIGN PATENT DOCUMENTS

CN    1457793 A    * 11/2003

* cited by examiner

*Primary Examiner* — Susan Hoffman
(74) *Attorney, Agent, or Firm* — Matthias Scholl, PC; Matthias Scholl

(57) ABSTRACT

Disclosed are methods of enhancing neurocognitive function by administering of American Ginseng. Preferred dosages in the range of 5 to 50 mg total genosides enhance cognitive function—including, improvement of working memory (WM) performance, attentional performance (e.g., Choice Reaction Time accuracy), and calmness.

10 Claims, 2 Drawing Sheets

APPLICATION OF AMERICAN GINSENG TO ENHANCE NEUROCOGNITIVE FUNCTION

The present application is a divisional of U.S. patent application Ser. No. 12/435,343, titled "Application of American Ginseng to Enhance Neurocognitive Function," filed on May 4, 2009, now abandoned, which is hereby incorporated by reference herein in its entirety.

FIELD OF THE INVENTION

The present invention relates to the use of American Ginseng (*Panax quinquefolius*) to increase neurocognitive function (for example, memory, attention, and calmness, among others).

BACKGROUND OF THE INVENTION

The term "Ginseng" is generally used to refer to the species of the genus *Panax* of the family Araliaceae. Extracts of Asian Ginseng (*Panax ginseng*) have been used for millennia in Traditional Chinese Medicine for the prevention and treatment of a variety of diseases, and have been also used as general health elixirs and performance enhancers (including in the neurocognitive area). There is a growing body of evidence to support Asian Ginseng as a cognitive enhancer. American Ginseng (*Panax quinquefolius*) is also in the family Araliaceae, although until now the cognition-enhancing properties of American Ginseng have not been known.

Research evaluating behavioural effects of chronic administration of Asian Ginseng in animals has demonstrated attenuation of learning deficits in aged rodents (Wen, T. C. et al. (1996) "Ginseng root prevents learning disability and neuronal loss in gerbils with 5-minute forebrain ischemia," *Acta Neuropathol* 91:15-22; Zhao, R. & McDaniel, K. (1998) "Ginseng improves strategic learning by normal and brain-damaged rats," *NeuroReport* 9:1619-1624; Nitta, H. et al. (1995) "*Panax Ginseng* extract improves the scopolamine-induced disruption of 8-arm radial maze performance in rats" *Biol Pharm Bull* 18:1439-1442). In one study, not only was learning improved in gerbils with learning deficits associated with forebrain ischemia, but Asian Ginseng was also neuroprotective, rescuing hippocampal CA1 pyramidal neurons (Wen et al. 1996). In young rodents, Asian Ginseng-related improvements may follow an inverted U-dose response. Mice administered 3, 10, 30, 100 & 300 mg/kg Asian (extract G115) improved performance following 10 mg/kg in an inverted-U-dose-response manner. However this effect was observed for a selection of tasks only (Petkov, V. D. & Mosharrof, A. H. (1987) "Effects of standardized Ginseng extract on learning, memory and physical capabilities," *Am J Chin Med* 15:19-29). Studies have observed cognitive benefits over a range of dosages of Asian Ginseng, ranging from 10 mg/kg to 150 mg/kg (Petkov & Mosharrof, 1987; Petkov V. D. et al. (1993) "Memory effects of standardized extracts of *Panax Ginseng* (G115), Ginkgo biloba (GK 501) and their combination Gincosan (PHL-00701)," *Planta Med* 59:106-114), with some doses appearing to impair cognitive function. For example, Petkov & Mosharrof (1987) found that higher dosages of Asian Ginseng G115 (300 mg/kg) impaired conditioned reflex activity in rats. The dose-response profile of Asian Ginseng is further complicated by variations in methods of assessment, age and dosage (Petkov et al. 1993)

In the few chronic administration studies on human subjects beneficial effects of Asian Ginseng were observed in cognitive deficit populations. For example, Neri et al. administered an Asian Ginseng-containing vitamin complex or placebo for 9 months and examined performance of participants suffering from age-related cognitive decline (Neri, M. et al. (1995) "Influence of a double blind pharmacological trial on two domains of well being in subjects with age associated memory impairment," *Arch Gerontol Geriatr* 21:241-252). They observed improvement of mnemonic performance following Asian Ginseng. In non-insulin dependent diabetic patients 8-week administration of 200 mg Asian Ginseng improved psychophysical performance compared to placebo (Sotaniemi, E. A. et al. (1995) "Ginseng therapy in non-insulin-dependent diabetic patients," *Diabetes Care* 18:1373-1375). One study aimed to assess the effects of an Asian Ginseng supplement combination 'Gericomplex' (Asian Ginseng, vitamins, minerals and trace elements) on mental health and wellbeing of geriatric patients. Two capsules were taken daily for 8 weeks, but they failed to observe any cognitive enhancement by the intervention (Thommessen, B. & Laake, K. (1996) "No identifiable effect of Ginseng (Gericomplex) as an adjuvant in the treatment of geriatric patients," *Aging* 8:417-420). In healthy individuals over the age of 40 Sorensen & Sonne administered 400 mg of standardized Asian Ginseng extract for 8 to 9 weeks and observed significantly faster reaction times compared to placebo (Sorensen, H. & Sonne, J. (1996) "A double masked study of the effects of Ginseng on cognitive functions," *Curr Ther Res* 57:959-968). In healthy young individuals D'Angelo et al. found that following 12 weeks of treatment of either 100 mg of Asian Ginseng (G115) or placebo (taken twice daily), patients administered Asian Ginseng demonstrated mental arithmetic (D'Angelo, L. et al. (1986) "A double-blind, placebo-controlled clinical study on the effect of a standardized Ginseng extract on psychomotor performance in healthy volunteers," *J Ethnopharmacol* 16:15-22). However these data should be interpreted with caution as the above studies have been criticized on a number of methodological issues such as inadequate sample sizes, non-standardised treatments, and inadequate research designs and statistical analysis (see Bahrke, M. S. & Morgan, W. P. (1994) "Evaluation of the ergogenic properties of Ginseng," *Sports Med* 18:229-248; Bahrke, M. S. & Morgan, W. P. (2000) "Evaluation of the ergogenic properties of Ginseng: an update," *Sports Med* 298:113-133; Kennedy, D. O. et al. (2003) "Modulation of mood and cognitive performance following administration of single doses of Melissa officinalis (Lemon balm) with human CNS nicotinic and muscarinic receptor binding properties," *Neuropsychopharmacology* 28: 1871-1881).

In a series of studies assessing the effects of acute administration of Asian Ginseng on cognition in young healthy individuals, enhancement by Asian Ginseng was observed largely for 'secondary memory' (a composite of four secondary memory tasks). (Kennedy et al. 2003; Scholey, A. B. & Kennedy, D. O. (2002) "Acute, dose-dependent cognitive effects of Ginkgo biloba, *Panax ginseng* and their combination in healthy young volunteers: differential interactions with cognitive demand," *Hum Psychparmacol Clin* 17:35-44). In the first study, doses of 200, 400 and 600 mg Asian Ginseng (G115) were administered (Kennedy, D. O., et al. (2001a) "Differential, dose-dependent changes in cognitive performance and mood following acute administration of Ginseng to healthy young volunteers." *Nutr Neurosci* 4:295-310). Enhancement of 'secondary memory' was found following 400 mg at four post-dose testing sessions, while the lower and higher dosage diminished performance for 'speed of attention' (Id.)

In a further study, assessing combinations of Asian Ginseng and Ginkgo (ratio 100:60) at dosages of 320, 640, 960 mg, a similar pattern was observed (Kennedy, D. O. et al.

(2001b) "Differential, dose dependent changes in cognitive performance following acute administration of a Ginkgo biloba/*Panax Ginseng* combination to healthy young volunteers," *Nutr Neurosci* 4:399-412). With performance of secondary memory being improved by 960 mg, and reduced performance on speed of attention for the other dosages (320 and 640 mg) (Id.). A later study, replicated the finding that a 400 mg dosage improves "secondary memory." Further study also assessed the effect of 200, 400 and 600 mg Asian Ginseng on mental arithmetic performance, where cognitive demand was manipulated (Kennedy, D. O., et al. (2002a) "Modulation of cognition and mood following administration of single doses of Ginkgo biloba, Ginseng and a Ginkgo/Ginseng combination to healthy young adults," *Physiol Behav* 72:953-964). Again this task was improved by a 400 mg dosage but only for the most demanding version of the task (Serial Sevens) (Reay, J. L. et al. (2005) "Single doses of *Panax ginseng* (G115) reduce blood glucose levels and improve cognitive performance during sustained mental activity," *J Psychopharmacol.* 19(4):357-65; Reay, J. L. et al. (2006) "Effects of *Panax ginseng*, consumed with and without glucose, on blood glucose levels and cognitive performance during sustained 'mentally demanding' tasks," *J Psychopharmacol.* 20(6):771-81.) It appears to be the case that Asian Ginseng or its constituents are capable of producing tangible cognitive enhancing effects and that for Asian Ginseng 200 or 400 mg appears to be an optimal dose for young healthy adults when administered acutely prior to a cognitive test.

The constituents of Asian Ginseng (*Panax ginseng*) that are thought to contribute to its bioactivity are the ginsenoside saponins. Ginsenosides can be classified into three groups on the basis of their chemical structure; the Panaxadiol group (Rb1, Rb2, Rb3, Rc etc.), Panaxatriol group (Re, Rf, Rg1, Rg2, Rh1), and the oleanolic acid group (e.g. Ro).

American Ginseng (*Panax quinquefolius*), by contrast, has its own characteristic profile exhibiting a high expression of the Ginsenoside Rb1. The American Ginseng extract used in the present study contains 11.65% Ginsenosides (Rb1 (5.68%), Re (2.05%), Rc (1.86%), Rd (1.47%), Rb2 (0.029%), Rg1 (0.027%)).

Many of these ginsenosides have been isolated and evaluated for pharmacological effects in animal and human models. They have been reported to exert effects on the cholinergic system; isolated Rb1 was both observed to increase synaptosomal choline uptake, and stimulate acetylcholine release (Benishin, C. G. et al. (1991) "Effects of ginsenoside RbI on central cholinergic metabolism," *Phlrmanacology* 42:223-229; Benishin, C. G. (1992) "Actions of ginsenoside RbI on choline uptake in central cholinergic nerve endings," *NeInrochenm* 21:1-5). Ginsenosides Rg1 and Rb1 have also been found to elicit marked alterations in brain serotonin concentrations (Zhang, J. T. et al. (1990) "Preliminary study on antiamnestic mechanism of ginsenoside RgI and RbI," *Chin Med J* 103:932-938). Furthermore Salim found that in rat brains Rb1 increased expression of choline acetyltransferase and nerve growth factor messenger RNA (Salim, K. N. et al. (2004) "Ginsenoside RbI regulates ChAT, NGF and trkA mRNA expression in rat brain," *Braini Res Mol Brait Res* 1997 47:177-182). Other ginsenosides have also been reported to effect specific physiological mechanisms, ginsenoside Rd has been reported to affect corticosterone secretion (Hiai, S. et al. (1983) "Evaluation of corticosterone secretion-inducing activities of ginsenosides and their prosapogenins and sapogenins," *Cltern Pharmii Blill* (Tokyo) 1:168-174) and ginsenosides Rd and Re may inhibit synaptosomal uptake of norepinephrine, dopamine, serotonin and GABA (Tsang, D. et al., (1985) "Ginseng saponins: influence on neurotransmitter uptake in rat brain synaptosomes," Planta Med 47:221-224). Furthermore in vivo modulation of LTP in the hippocampal formation by Ginsenoside Rb1 has been observed in rats (Abe, K. et al. (1994) "Differential effects of ginsenoside Rb1 and malonylginsenoside Rb1 on long-term potentiation in the dentate gyrus of rats," *Brain Res.* 649(1-2):7-11.)

With respect to evaluating potential cognitive enhancement by whole extract American Ginseng (*Panax quinquefolius*), one study observed that scopolamine induced amnesia in Sprague-Dawley rats was attenuated by administration of American Ginseng. American Ginseng attenuated the scopolamine-associated decrement on performance of the Morris water maze task (spatial learning) and increased choline uptake in synaptosomal preparations (Sloley, B. D., et al. (1999) "American Ginseng extract reduces scopolamine induced amnesia in a spatial learning task," *J Psychiatry Neurosci* 24:442-452). However, studies assessing the psychogenic benefits of American Ginseng are rare.

SUMMARY OF THE INVENTION

Until now, the beneficial effects of American Ginseng on cognitive function have not been known. The present invention provides methods of using American Ginseng to enhance cognitive function—including, improvement of working memory, attention, and calmness, among others. The inventors have discovered that administering American Ginseng improves working memory (WM) performance: spatial span was improved by all doses at all testing times; other WM tasks were differentially improved by the 200 mg dose (with time- and task-specific benefits associated with other doses). Also, attentional performance (Choice Reaction Time accuracy) was significantly improved by 100 mg at all times and by 200 and 400 mg after 6 h. Furthermore, the 100 mg dose was associated with significantly enhanced "calmness" at 3 h and 6 h.

BRIEF DESCRIPTION OF THE DRAWINGS

Further features, advantages and characteristics of the present invention will become apparent to a person of ordinary skill in the art in view of the following detailed discussion of preferred embodiments of the present invention, made with reference to the drawings annexed, in which.

DETAILED DESCRIPTION OF THE INVENTION

Figure 1:
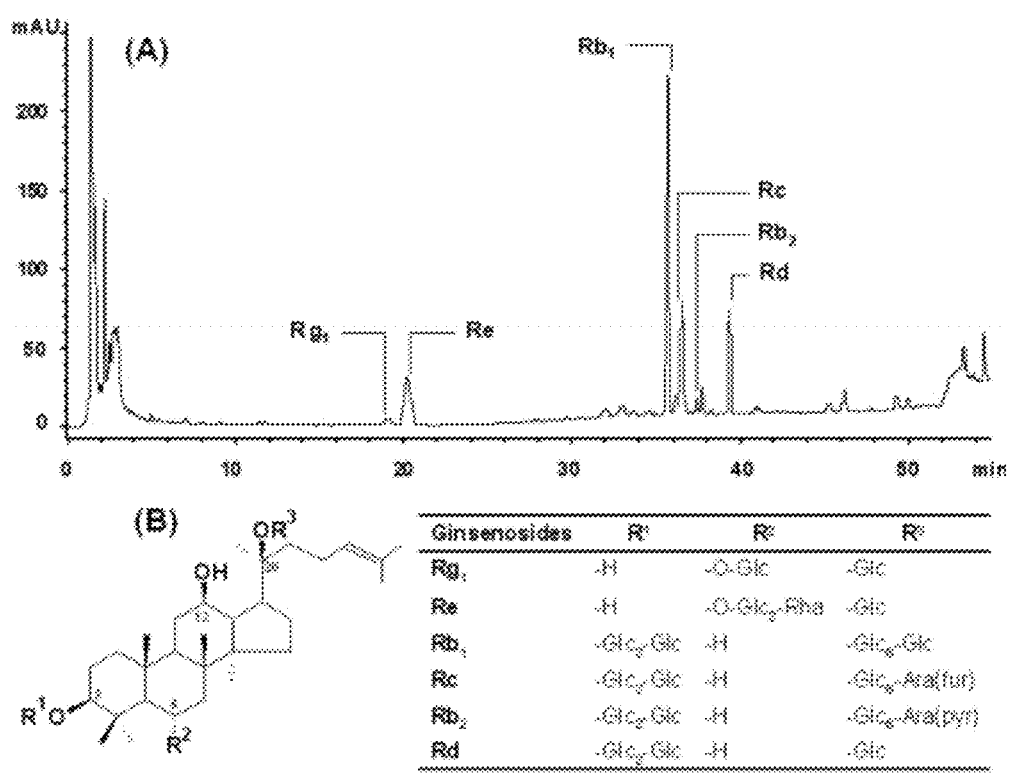
FIG. 1 illustrates: (A) Chromatogram of the American ginseng (*Panax quinquefolius*) extract; and (B) Structures of ginsenosides.

The present invention relates to the novel discovery that acute consumption of *Panax quinquefolius* (American Ginseng) can improve cognitive performance and increase calmness in healthy young adults. All doses of *Panax quinquefolius* were found to improve some aspect of cognition.

In addition to being administered whole, American Ginseng can be administered as an extract, powder, or in other modified form. Based on the modifications, the amount of ginsenosides present may vary. For example, Naturex produces milled root form of American Ginseng (PurePowder), which contain total ginsenosides content between about 3 and 7% (usually standardized to 5%). Naturex also produces an extract of American Ginseng, which contain total ginsenosides content between amount 7 to 16% (usually standardized to 10%). The distribution of ginsenosides is similar in all products and a person of ordinary skill in the art would understand how to make other powders, extracts, and modified products containing ginsenosides. The composition described below in connection with a preferred embodiment of the present invention is an extract of American Ginseng containing 11.65% of total ginsenosides.

American Ginseng can be administered in a range of doses, which can benefit different domains of cognitive function. All doses appeared have some cognitive effects with optimal doses appearing to have some task-specificity. Perhaps the most striking and surprising result was that all three doses improved Corsi block performance compared to placebo at all post-dose time points with the most beneficial effects being observed for the lower two doses. A preferred embodiment of the present invention involves improving Immediate Word Recall accuracy and Numeric Working Memory speed by administering a 200 mg dose. Another preferred embodiment involves improving Alphabetic Working Memory speed by administering 100 mg or 400 mg doses. Another preferred embodiment involves improving Choice Reaction Time accuracy by administering a 100 mg or 400 mg dose 1 hour in advance of desired results. A further preferred embodiment for improving Choice Reaction Time involves administering 100 mg at least 3 hours before desired results, and further preferred to be administered 6 hours before desired results.

For improving Immediate Word Recall and Numeric Working Memory, preferred embodiments involve a dose of 200 mg. For other tasks (Choice Reaction Time, Alphabetic Working Memory and the Corsi block task) both high and low dosages appeared to improve performance. It is further preferred that the American Ginseng be administered 6 hours in advance of desired results. As used herein, the term "high dose" refers to a dosage of between 400 and 500 mg, and the term "low dose" refers to a dosage of between 50 and 400 mg.

American Ginseng also has beneficial effects on mood in healthy young adults. For example, 100 mg of *Panax quinquefolius* improves feelings of calmness in a time dependent manner. This effect was significantly higher 3 h and 6 h following administration compared to placebo. In contrast, a number of studies have assessed the effect of Asian Ginseng (*Panax ginseng*) on mood using the Bond Lader mood scale (Kennedy et al. 2001a; Kennedy et al. 2001b; Kennedy et al. 2002a; Kennedy et al. 2003; Scholey & Kennedy 2002), the same scale used in connection with the present invention. These studies all assessed the acute effects of Asian Ginseng on mood. One study demonstrated an effect of Asian Ginseng on mood in that at 200 and 400 mg dosages feelings of alertness declined 6-hours following treatment of Asian Ginseng (Kennedy et al. 2001a).

Another study assessed the effects of acute administration of Asian Ginseng on fatigue in healthy young individuals (Reay et al., 2005) and observed that subjective feelings of mental fatigue were ameliorated in a time-dependent manner by 200 mg Ginseng during sustained intense cognitive processing. (The present invention found that self-rated calmness was reduced over the course of testing following placebo and 100 mg American Ginseng extract essentially produced increased feeling of calmness, possibly tapping into feelings of fatigue which increased with cognitive testing and were stabilized by 100 mg treatment.) It may be that effects were most pronounced at the later time point due to increasing stress levels over the testing phase, in which case we might attribute an adaptogenic effect might be attributed to the ginseng extract. Previous research in rodents has shown that Ginseng saponins and Ginsenoside Rb1 inhibit the stress-induced increases in plasma corticosterone (Kim, H. S. et al. (1998) "Effects of ginsenosides on Ca2+ channels and membrane capacitance in rat adrenal chromaffin cells," *Brain Res Bull.* 46(3):245-51.)

The present invention relates to the enhancement effects of American Ginseng (*Panax quinquefolius*) predominantly on working memory (WM) processes (Corsi block, and both Numeric and Alphabetic Working Memory). This also related to positive effects on short-term verbal declarative memory (Immediate Word Recall) and attention (Choice Reaction Time). WM and short-term memory systems are thought be localized to hippocampal and pre-frontal cortices. It is generally agreed that the hippocampus has an important role in the formation of new memories about experienced events such as episodic or autobiographical memory. While the pre-frontal cortex deals with higher-order working memory/executive functions including manipulating working memory (Gabrieli, J. D. (1998) "The role of left prefrontal cortex in language and memory," *Proc Natl Acad Sci USA* 95:906-913; Goldman-Rakic, P. S. (1996) "The prefrontal landscape: Implications of functional architecture for understanding human mentation and the central executive [and discussion]," *Philosophical Transactions of the Royal Society of London, Series B: Biological Sciences* 351:1443-1453), it has been well documented that the cholinergic pathways projecting to the cerebral cortex and hippocampus play a key role in learning and memory and it has been argued that the brain cholinergic system is a specific target for cognitively enhancing agents (Giovannini, M. G. et al. (1995) "Differential regulation by N-methyl-D-aspartate and non-N-methyl-D-aspartate receptors of acetylcholine release from the rat striatum in vivo," *Neuroscience* 65(2):409-15.) A number of studies have identified cholinergic properties associated with isolated ginsenosides. A direct interaction between Rg2 and nicotinic receptor subtypes has been observed (Sala, F. et al. (2002) "Effects of ginsenoside Rg2 on human neuronal nicotinic acetylcholine receptors," *J Pharmacol Exp Ther.* 301(3):1052-59.) Moreover Benishin (1992) demonstrated modulation by Rb1 of acetylcholine release and reuptake, along with a number of choline uptake sites in the hippocampus, and to a lesser extent, the cortex. Both ginsenosides Rg1 (Zhang et al. 1990) and Rb1 (Salim et al. 2004; Zhang et al. 1990) have also been shown to increase choline acetyltransferase levels in rodent brains.

In animal research, one study observed that scopolamine-induced deficits are attenuated by American Ginseng (*Panax quinquefolius*) in Sprague Dawley rats (Sloley et al. 1999). Protection against scopolamine-induced amnesia by American Ginseng was most evident in trials where animals were required to remember the task learned the previous day. In this study it was also observed that American Ginseng increased choline uptake into synaptosomes prepared from rat brain. Also, in the human brain crude extracts of Asian Ginseng exhibited an affinity for both nicotinic and muscarinic receptors in cerebral cortex membranes, (Lewis, R. et al., "Non-ginsenoside nicotinic activity in ginseng species," *Phytother Res.* 13(1):59-64.)

As discussed previously, the American Ginseng extract profile has 2-3 times the ginsenoside content than the more commonly researched Asian Ginseng, with the highest expression of Rb1 and Re. The cholinergic system is one potential central mechanism of action on the enhancement of memory by American Ginseng.

The inventors also assessed the acute effects of American Ginseng (*Panax quinquefolius*) on glucoregulation on young healthy adults. Vuksan et al (2000) previously observed that 300 mg *Panax quinquefolius* lowered blood glucose levels during a glucose challenge in both healthy and diabetic subjects. (Vuksan, V. et al. (2000a) "American ginseng (*Panax quinquefolius* L) reduces postprandial glycemia in nondiabetic subjects and subjects with type 2 diabetes mellitus," *Arch Intern Med.* 160(7):1009-13.) Other studies also observed similar results: American Ginseng appeared to have significant hypoglycaemic action in rodents (Oshima, Y. et al. (1987) "Isolation and hypoglycaemic activity of quinquefolans A, B, and C, glycans of *Panax quinquefolium* roots," *J Nat Prod* 50:188-190; Martinez, B. & Staba, E. J. (1984) "The physiological effects of *Aralia, Panax* and *Eleutherococcus* on exercised rats," *Jpn J Pharmacol* 35:79-85). In humans, American Ginseng also reduced blood glucose levels following a 25-g glucose challenge in both diabetic patients who had ingested 300, 600, and 900 mg and non diabetics administered 100, 200, and 300 mg (Vuksan, V. et al., 2000a; Vuksan, V. et al. (2000b) "Similar postprandial glycemic reductions with escalation of dose and administration time of American Ginseng in type 2 diabetes," *Diabetes Care* 23:1221-1226; Vuksan, V. (2006) "Korean red Ginseng (*Panax Ginseng*) improves glucose and insulin regulation in well controlled type 2 diabetes: results of a randomized, double-blind, placebo-controlled study of efficacy and safety," *Nutr Metab Cardiovasc Dis* 18:46-56) (Vuksan et al. 2000a). The present invention, however, shows that, at least at the dosages used here (100 mg, 200 mg, and 400 mg), American Ginseng has no detectable effect on blood glucose levels.

Overall the present invention is the first to demonstrate cognitive and mood enhancement following *Panax quinquefolius* administration. Cognition-enhancing effects of the present invention were observed across a range of cognitive modalities at a range of dosages. The lack of glycaemic effects also highlights important methodological differences between existing literature and the present invention, and thus one of ordinary skill in the art will more fully understand how American Ginseng's impact on glucose levels may be moderated.

EXAMPLES

The results of each of the following examples were tested by a randomized, double-blind, placebo-controlled, crossover trial (N=32 healthy young adults) to evaluate the acute mood, neurocognitive and blood glucose effects of 3 doses (100, 200, 400 mg) of an American ginseng extract (standardized to 10.65% ginsenosides) compared to placebo. On study days (separated by a >7-day wash-out) participants underwent a baseline assessment of mood, cognitive function and blood glucose. They then took the day's treatment followed by the same assessments 1, 3 and 6 hours later. Statistical analysis used a two-way (Treatment×Time) ANOVA followed by pre-planned comparisons of each dose's effects compared with placebo at each time point.

Participants

Thirty two participants (16 male, 16 female) were recruited via advertisements in local newspapers and university bulletin boards to take part in the study. Ages ranged from 18 to 40 years (M=25.2, SD=4.97). All participants reported that they were in good health, not taking any drugs or medications (excluding the contraceptive pill), had no known food allergies and were non smokers.

They completed an initial health screening questionnaire which excluded participants with a number of medical conditions (e.g. diabetes, hypoglycaemia, psychiatric disorders, epilepsy, and gastrointestinal disorders) or who were on prescribed medications, were pregnant or lactating. They were advised to refrain from taking any vitamins, other herbal supplements and over the counter medicines for the whole period of study. On the testing days, participants were advised to abstain from consuming alcohol, caffeine products and energy drinks. They were required to eat a light breakfast (toast or cereal) at least 2 hours before the onset of the experiment and were provided with sandwich for lunch (with either chicken and salad, or cheese and salad). The study was approved by the Swinburne University Human Research Ethics Committee and all participants gave written informed consent. The study was conducted according to the Declaration of Helsinki. Volunteers received a 200 AUD cheque at the end of the study for their participation.

Treatments

The coated capsules utilized in the study contained a standardized to 10% Ginsenosides commercial extract of *Panax quinquefolius* (American Ginseng) prepared and provided by Naturex.

Extract Preparation

The roots of American ginseng (*Panax quinquefolius*) were authenticated using macroscopic, microscopic, and high performance thin layer chromatography techniques (Reich, E. & Schibli (2007) "A In: High-Performance Thin-Layer Chromatography for the Analysis of Medicinal Plants," ISBN: 9781588904096, Thieme Medical Publishers Inc., New York, N.Y.). The American ginseng extract was obtained through an industrial process (Naturex, USA, Reference: 331350, Lot number: E15/05/D8). First, the ginseng roots were ground to be between ¼ and ½ inch, and then the ground roots were soaked three times during five hour intervals in an ethanol/water (75/25, v/v) solution at 40° C. After filtration, the clarified solution was then concentrated under vacuum at 45° C. The three pools were combined and concentrated again until the total solids on dry basis were around 60%. This is the Native Extract, which was then mixed with maltodextrin as a carrier and spray dried to obtain a fine powder. The moisture content in the extract was less than 5%. After extraction, the sample was analyzed for its content of pesticides (USP. General Chapters: <561> Articles of Botanical Origin. Test for Pesticides. USP-31-NF26 S1, Rockville, Md. 2008) and heavy metals (method 993.14, AOAC, Official Methods of Analysis (2005) 18th Ed. AOAC International, Gaithersburg, Md.) at Covance Laboratories (Madison, Wis., USA) for compliance. The American ginseng extract was found to be below the Maximum Residue Limits established for pesticides and heavy metals (Durgnat, J. M. et al. (2005) "Quality and safety assessment of ginseng extracts by determination of the contents of pesticides and metals," *Food Additives & Contaminants* 22:1224-1230).

The American ginseng extract used in this clinical trial contained 0.28% of $Rg_1$, 2.06% of Re, 5.69% of $Rb_1$, 1.87% of Rc, 0.29% of $Rb_2$, and 1.48% of Rd. The total ginsenosides, calculated as the sum of above individual ginsenosides, represented 11.65% in the American ginseng extract. As expected, the ginsenoside Rf was not found (Harkey, M. R. et al. (2001) "Variability in commercial ginseng products: an analysis of 25 preparations," *Am J Clin Nut* 73:1101-1106). The ginsenoside Rf is not present in American ginseng but it is present in Asian ginseng (*Panax ginseng*), and is used as a marker to determine adulterations in American ginseng. The chromatogram of the American ginseng extract and the structures of its ginsenosides is presented in FIG. 1.

Initial one-way analyses on each cognitive and mood measure revealed no significant baseline differences between conditions confirming that post-treatment effects were not attributable to change differences in baseline performance. Significant effects associated with treatments are presented in FIG. 2.

Example 1

Administering American Ginseng served to improve Choice Reaction Time in the following situation.

Choice Reaction Time: The arrow pointing to the left or right was presented in the centre of the screen at irregular time intervals. The volunteer makes a response with 'left' and 'right' cursor buttons to arrows pointing to the left or right respectively as quickly as possible. Each of the 15 stimuli remained on screen until the key press was registered. The inter-stimulus interval randomly varying between 1 and 3 seconds. Outcomes were accuracy (% correct) and reaction time (ms).

Four Choice Reaction Time: A replica of the four direction arrow keys found at the bottom and to the right of the computer keyboard appeared on the screen. The participants were instructed to make a response as quickly and as accurately as possible with 'left', 'right', 'up' and 'down' cursor keys corresponding to the arrow being illuminated on the screen one at a time, pointing randomly to the left, right, up or down. Each of the 16 stimuli remained on screen until the key press was registered. The inter-stimulus interval randomly varying between 1 and 3 seconds. The task was scored for accuracy (% correct) and reaction time (ms).

For Choice Reaction Time accuracy there was a significant main effect of treatment [$F(3,162)=3.406$, $p=0.021$]. Comparisons of each dose at each time point revealed significant improvements associated with the 100 mg dose at all three time points. There were also significant improvements for 200 mg at 1 hr and both 200 mg and 100 mg at 6 hrs ($P<0.05$ in all cases).

Example 2

Administering American Ginseng served to improve Immediate Word Recall in the following situation.

Word Presentation: Ten common English words appropriate for the age range of participants were drawn from http://www.math.yorku.ca/SCS/Online/paivio/. Words were matched for linguistic familiarity, concreteness and frequency and presented in sequence on the monitor for the participant to remember at the commencement of the battery. Stimulus duration was 1 s, as was the inter-stimulus interval.

Immediate word recall: The participant was allowed 60 s to write down as many of the retained words as possible. The task was scored for number of correct answers, errors and intrusions and the resulting score was converted into a percentage.

Figure 2:
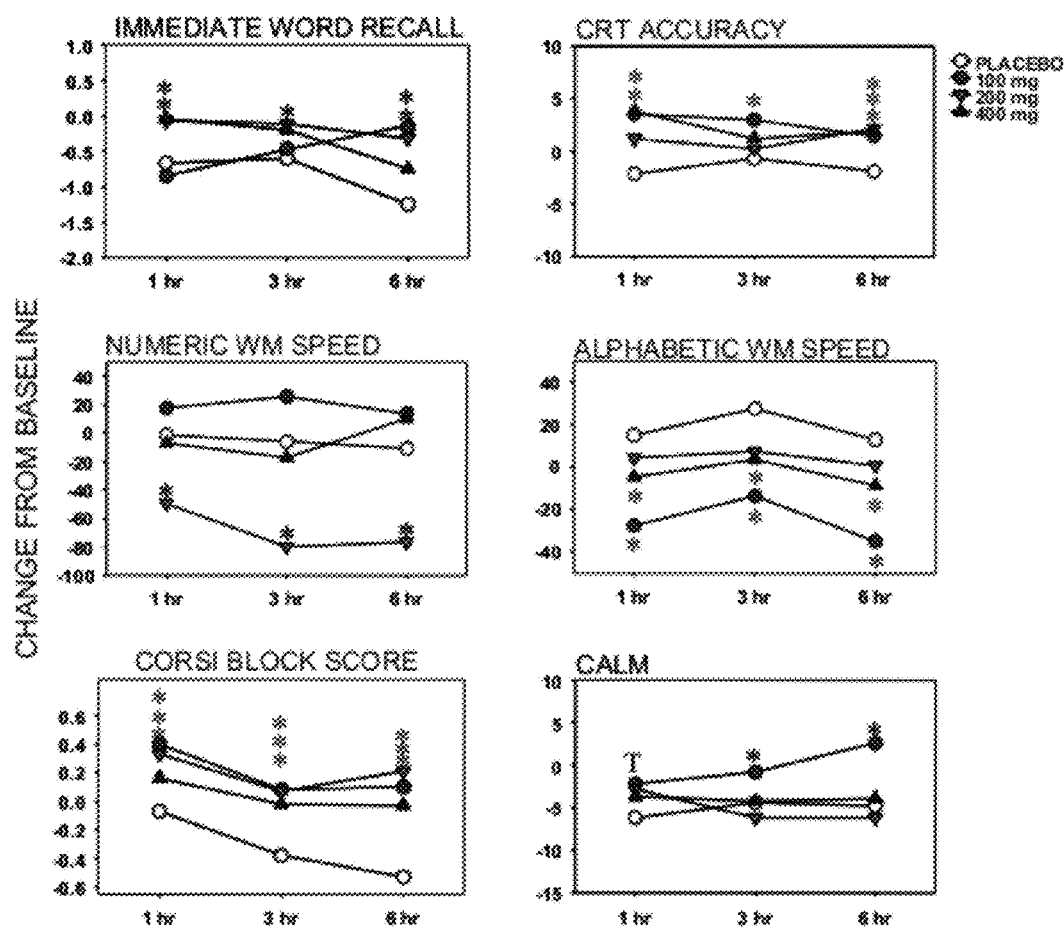
FIG. 2 illustrates the significant effects of *Panax quinquefolius* on cognitive function and mood. Graphs depict mean change-from-baseline scores following a placebo and 100 mg, 200 mg and 400 mg of a standardised extract. Significant differences from placebo at each time point are indicated (*, $p<0.05$)

There was a significant Treatment×Time interaction [$F(6, 174=2.399$, $p=0.03$)]. Comparisons of each dose at each time point revealed significant improvements associated with the 200 mg dose at all three time points. The were also significant improvements for 400 mg at 1 hr and 100 mg at 6 hr only ($p<0.05$ in all cases). Results are shown in FIG. 2.

Example 3

Administering American Ginseng served to improve Numeric Working Memory speed in the following situation.

Numeric Working Memory: A series of five digits was presented on the computer screen sequentially for the participants to hold in their memory. This is followed by a series of 30 probe digits. The participants decided whether or not the digit was from the original series and indicated their choice by pressing corresponding keys labelled 'YES' and 'NO'. This was repeated three further times with different stimuli sets. Reaction times (ms) and accuracy (% correct) were measured.

There was a significant main effect of Treatment for Numeric Working Memory speed. Comparisons of each dose at each time point revealed significant improvements associated with the 200 mg dose at all three time points. ($p<0.05$ in all cases).

Example 4

Administering American Ginseng improved Alphabetic Working Memory in the following situation.

Alphabetic Working Memory: This was similar to the numeric working memory but using letters. A series of 5 letters appeared on the screen for participant to remember. After 4 seconds the letters disappeared and were followed by a series of 30 probe letters. Participants were instructed to indicate whether the target letter had appeared in the original list of five letters by pressing corresponding 'YES' or 'NO' key as quickly as possible. The measures were the percentage of the correctly identified stimuli and the average reaction time (ms).

There was a trend for a main effect of Treatment for Alphabetic Working Memory [$F(3,60)=2.7$, $p=0.063$]. This trend merited further exploration and comparisons of each dose at each time point revealed significant improvements associated with the 100 mg and 400 mg doses at all three time points ($p<0.05$ in all cases).

Example 5

Administering American Ginseng served to improve spatial span in the following situation.

Corsi Blocks: The Corsi Block-Tapping Task (initially developed by Corsi, 1972) is a span task and a visuospatial analogue to the digit span of verbal short-term memory (Lezak, 1995). A computerized version of the Corsi blocks task was employed in the study. A series of squares appeared on the screen. A number of these illuminated sequentially in quasi-random order. The volunteer then attempted to repeat the pattern by clicking the boxes in the same order with the mouse and cursor. The difficulty increases from 4 blocks upwards. The task gives a measure of spatial span as well as speed of responding.

There was a significant main effects of Treatment on mean Corsi block score [$F(3,114)=2.925$, $p=0.041$]. Comparisons of each dose at each time point revealed significant improvements associated with the all doses at all time points. ($p<0.05$ in all cases).

Example 6

Administering American Ginseng served to improve calmness in the following situation.

Depression Anxiety and Stress Scale (DASS; Lovibond & Lovibond, 1995): The shortened 21-item version of the DASS was used to assess three negative affective states of depression, anxiety and stress on seven-item scales. The Depression subscale (DASS-D) measures symptoms relating to dysphoric mood (e.g. sadness), for example "I couldn't seem to experience any positive feeling at all." The Anxiety subscale (DASS-A) assesses symptoms associated with physiological hyperarousal such as autonomic arousal, for example "I felt I was close to panic." The Stress subscale (DASS-S) assesses symptoms associated with nervous arousal, for example "I tended to over-react to situations." Participants were required to indicate on a 4-point scale whether each statement applied to them not at all, to some degree, a considerable degree, or most of the time. Scores were calculated by summing the scores of the appropriate items. Good internal consistency and validity for the DASS have been found with samples of clinical patients and non-clinical volunteers (Anthony et al., 1998).

State-Trait Anxiety Inventory (STAI) The State-Trait Anxiety Inventory (STAI) (Speilberger et al, 1969) comprises of two scales. The 'State' (STAI-S) subscale is a widely used instrument for measuring fluctuating levels of anxiety. The subscale contains 20 statements (e.g. 'I am calm'). Participants rate how much they feel like each statement at the time of making the response by marking a 4-point scale ranging from "not at all" to "very much so." The "Trait' (STAI-T) subscale comprises 20 different statements (e.g. "Some unimportant thought runs through my mind and bothers me"). Participants are asked to indicate how they generally feel on a scale ranging from "almost never" to "almost always." Scores on both sections of the STAI range from 20 to 80, with higher scores indicating more anxiety.

Symptom checklist: The symptom checklist consisted of 28 physiological/psychological problems people might have (e.g. I feel dizzy, I have a dry mouth, I feel anxious more than usual). Participants indicated how much the problem had bothered them in the last 7 days including today using a 5-point scale from "not at all" to "very much so."

There was a single significant effect on mood measures. The Treatment×Time interaction on self-rated calmness was significant [F6,150=2.345, p=0.034]. Comparisons of each dose at each time point revealed significant improvements associated with the 100 mg dose at 3 h and 6 h only (p<0.05 in both cases).

One skilled in the art will appreciate that the present invention can be practiced by other than the embodiments disclosed herein, which are presented for purposes of illustration, and not of limitation.

We claim:

1. A method of enhancing cognitive performance in working memory of a human subject in need thereof, the method comprising administering to said human subject a composition comprising American ginseng extract and a carrier, in an effective amount to enhance the cognitive performance, wherein said American ginseng extract comprises 3 parts of ginsenoside Rb2; 3 parts of ginsenoside Rg1; 22 parts of ginsenoside Re; 61 parts of ginsenoside Rb1; 20 parts of ginsenoside Rc and 16 parts of ginsenoside Rd; and said ginsenoside Rb2, said ginsenoside Rg1, said ginsenoside Re, said ginsenoside Rb1, said ginsenoside Rc, and said ginsenoside Rd constitute 11.65% of the weight of said American ginseng extract.

2. The method of claim 1 wherein said American ginseng extract is free of ginsenoside Rf.

3. The method of claim 1 wherein the effective amount comprises about 23.30 mg of said ginsenoside Rb2, said ginsenoside Rg1, said ginsenoside Re, said ginsenoside Rb1, said ginsenoside Rc, and said ginsenoside Rd in total.

4. The method of claim 1, wherein the method further comprises assessing said cognitive performance by administering Numeric Working Memory test to said human subject.

5. The method of claim 4 wherein said human subject is administered said composition between 1 and 6 hours prior to the step of assessing said cognitive performance.

6. The method of claim 1, wherein the carrier is maltodextrin.

7. A method of enhancing cognitive performance in numeric working memory within 6 hours after an administration of American ginseng extract, the method comprising administering about 200 mg of American ginseng extract to a human subject in need of enhancing cognitive performance in numeric working memory within 6 hours after an administration of American ginseng extract, wherein said American ginseng extract comprises about 0.2% of ginsenoside Rb2; about 0.2% of ginsenoside Rg1; about 2.0% of ginsenoside Re; about 5.0% of ginsenoside Rb1; about 2.0% of ginsenoside Rc and about 1.4% of ginsenoside Rd.

8. The method of claim 7 wherein said American ginseng extract is free of ginsenoside Rf.

9. The method of claim 7, wherein the method further comprises assessing said cognitive performance by administering Numeric Working Memory test to said human subject.

10. The method of claim 9, wherein said American ginseng extract comprises about 23.30 mg of said ginsenoside Rb2, said ginsenoside Rg1, said ginsenoside Re, said ginsenoside Rb1, said ginsenoside Rc, and said ginsenoside Rd in total; and wherein said human subject is administered said American ginseng extract between 1 and 6 hours prior to the step of assessing said cognitive performance.

* * * * *